US006228954B1

(12) United States Patent
Kaplan et al.

(10) Patent No.: US 6,228,954 B1
(45) Date of Patent: *May 8, 2001

(54) BLENDS OF GLYCOLIDE AND/OR LACTIDE POLYMERS AND CAPROLACTONE AND/OR TRIMETHYLENE CARBONATE POLYMERS AND ABSORABABLE SURGICAL DEVICES MADE THEREFROM

(75) Inventors: Donald S. Kaplan, Weston; Matthew Hermes, Easton; Ross R. Muth, Brookfield; John Kennedy, Stratford, all of CT (US)

(73) Assignee: United States Surgical Corporation, Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/333,028

(22) Filed: Nov. 1, 1994

Related U.S. Application Data

(63) Continuation of application No. 08/101,272, filed on Aug. 2, 1993, now abandoned, which is a continuation of application No. 07/768,168, filed on Sep. 30, 1991, now abandoned, which is a continuation-in-part of application No. 07/654,234, filed on Feb. 12, 1991, now abandoned.

(51) Int. Cl.$^7$ ............................................. C08L 67/04
(52) U.S. Cl. .......................... 525/411; 525/413; 525/415; 606/77
(58) Field of Search ............................ 525/411, 413, 525/415; 606/77

(56) References Cited

U.S. PATENT DOCUMENTS

| | | |
|---|---|---|
| 2,668,136 | 2/1954 | Winkler . |
| 2,668,162 | 2/1954 | Lowe . |
| 2,683,136 | 7/1954 | Higgins . |
| 2,703,316 | 3/1955 | Schneider . |
| 2,758,987 | 8/1956 | Salzberg . |
| 3,225,766 | 12/1965 | Baptist et al. . |
| 3,268,486 | 8/1966 | Klootwijk . |
| 3,268,487 | 8/1966 | Klootwijk . |
| 3,297,033 | 1/1967 | Schmitt et al. . |
| 3,422,181 | 1/1969 | Chirgwin, Jr. . |
| 3,442,871 | 5/1969 | Schmitt et al. . |
| 3,463,158 | 8/1969 | Schmitt et al. . |
| 3,468,853 | 9/1969 | Schmitt et al. . |
| 3,531,561 | 9/1970 | Trehu . |
| 3,565,869 | 2/1971 | DeProspero . |
| 3,597,449 | 8/1971 | DeProspero et al. . |
| 3,620,218 | 11/1971 | Schmitt et al. . |
| 3,626,948 | 12/1971 | Glick et al. . |
| 3,636,956 | 1/1972 | Schneider . |
| 3,736,646 | 6/1973 | Schmitt et al. . |
| 3,739,773 | 6/1973 | Schmitt et al. . |
| 3,772,420 | 11/1973 | Glick et al. . |
| 3,773,919 | 11/1973 | Boswell et al. . |
| 3,781,349 | 12/1973 | Ramsey et al. . |
| 3,784,585 | 1/1974 | Schmitt et al. . |
| 3,792,010 | 2/1974 | Wasserman et al. . |
| 3,797,499 | 3/1974 | Schneider . |
| 3,839,297 | 10/1974 | Wasserman et al. . |
| 3,846,382 | 11/1974 | Ramsey et al. . |
| 3,867,190 | 2/1975 | Schmitt et al. . |
| 3,875,937 | 4/1975 | Schmitt et al. . |
| 3,878,284 | 4/1975 | Schmitt et al. . |
| 3,896,802 | 7/1975 | Williams . |
| 3,902,497 | 9/1975 | Casey . |
| 3,937,223 | 2/1976 | Roth . |
| 3,982,543 | 9/1976 | Schmitt et al. . |
| 4,033,938 | 7/1977 | Augurt et al. . |
| 4,045,418 | 8/1977 | Sinclair . |
| 4,057,537 | 11/1977 | Sinclair . |
| 4,060,089 | 11/1977 | Noiles . |
| 4,137,921 | 2/1979 | Okuzumi et al. . |
| 4,157,437 | 6/1979 | Okuzumi et al. . |
| 4,201,216 | 5/1980 | Mattei . |
| 4,243,775 | 1/1981 | Rosensaft et al. . |
| 4,246,904 | 1/1981 | Kaplan . |
| 4,273,920 | 6/1981 | Nevin . |
| 4,275,813 | 6/1981 | Noiles . |
| 4,279,249 | 7/1981 | Vert et al. . |
| 4,300,565 | 11/1981 | Rosensaft et al. . |
| 4,343,931 | 8/1982 | Barrows . |
| 4,402,445 | 9/1983 | Green . |

(List continued on next page.)

FOREIGN PATENT DOCUMENTS

| | | |
|---|---|---|
| 779291 | 7/1957 | (GB) . |
| 1034123 | 6/1966 | (GB) . |
| 1332505 | 10/1973 | (GB) . |
| 1414600 | 11/1975 | (GB) . |
| 2033411 | 5/1980 | (GB) . |
| 2102827 | 2/1983 | (GB) . |

OTHER PUBLICATIONS

Kulkarni, et al., J. Biomed. Master, Res, 1971, 5, pp. 169–181.

Vert, et al., Makromol. Chem., Suppl., 1981, 5, 30–41.

DK Gilding et al. "Biodegradable Polymers for Use in Surgery–Polyglycolic–Poly(actic acid) Homo–and Copolymers: 1" Polymer, vol. 20, pp. 1459–1464 (1979).

DF Williams (ed) Biocompatability of Clinical Implants Materials, vol. II Chapter 9: "Biodegradable Polymers" (1981).

Primary Examiner—David J. Buttner

(57) ABSTRACT

Polymer blends of glycolide and/or lactide homopolymer and/or glycolide/lactide copolymer and polycaprolactone and/or polytrimethylene carbonate homopolymer or copolymers thereof and absorbable surgical devices manufactured therefrom having improved mechanical properties, such as improved impact resistance and improved cyclic flex, are disclosed.

8 Claims, No Drawings

U.S. PATENT DOCUMENTS

| | | |
|---|---|---|
| 4,429,080 | 1/1984 | Casey et al. . |
| 4,539,981 | 9/1985 | Tunc . |
| 4,550,449 | 11/1985 | Tunc . |
| 4,595,713 | 6/1986 | St. John . |
| 4,605,730 | 8/1986 | Shalaby et al. . |
| 4,620,541 | 11/1986 | Gertzman et al. . |
| 4,624,256 | 11/1986 | Messur et al. . |
| 4,643,734 | 2/1987 | Lin . |
| 4,655,777 | 4/1987 | Dunn et al. . |
| 4,700,704 | 10/1987 | Jamiolkowski et al. . |
| 4,741,337 | 5/1988 | Smith et al. . |
| 4,744,365 * | 5/1988 | Kaplan ................................ 528/354 |
| 4,889,119 | 12/1989 | Jamiolkowski et al. . |
| 4,891,263 | 1/1990 | Kotliar et al. . |
| 4,905,680 | 3/1990 | Tunc . |
| 4,916,193 | 4/1990 | Tang et al. . |
| 4,920,203 | 4/1990 | Tang et al. . |
| 4,965,300 | 10/1990 | Eichenauer et al. . |
| 4,994,074 | 2/1991 | Bezwada et al. . |
| 5,037,950 | 8/1991 | Bezwada et al. . |
| 5,047,048 | 9/1991 | Bezwada et al. . |
| 5,061,281 | 10/1991 | Mares et al. . |
| 5,066,772 | 11/1991 | Tang et al. . |
| 5,080,665 * | 1/1992 | Jarrett ................................... 528/354 |
| 5,120,802 | 6/1992 | Mares et al. . |
| 5,145,945 | 9/1992 | Tang et al. . |
| 5,152,781 | 10/1992 | Tang et al. . |
| 5,185,408 | 2/1993 | Tang et al. . |
| 5,320,624 * | 6/1994 | Kaplan ................................ 525/411 |

* cited by examiner

BLENDS OF GLYCOLIDE AND/OR LACTIDE POLYMERS AND CAPROLACTONE AND/OR TRIMETHYLENE CARBONATE POLYMERS AND ABSORABABLE SURGICAL DEVICES MADE THEREFROM

CROSS REFERENCE TO RELATED APPLICATION

This is a continuation of application Ser. No. 08/101,272 filed Aug. 2, 1993 now abandoned, which is a File Wrapper Continuation Application of Ser. No. 07/768,168 filed Sep. 30, 1991, now abandoned.

This application is a continuation-in-part of U.S. application Ser. No. 07/654,234, filed Feb. 12, 1991 now abandoned.

BACKGROUND OF THE INVENTION

This invention relates to glycolide and/or lactide based polymer compositions and more particularly to polymer compositions which are blends of a glycolide and/or lactide homopolymer or glycolide/lactide copolymer and polycaprolactone homopolymer and/or polytrimethylene carbonate homopolymer and/or caprolactone or trimethylene carbonate copolymer, said polymer compositions being particularly useful in the manufacture of absorbable surgical devices.

Polymers and copolymers of, and surgical devices made from, lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,773,919, 3,781,349, 3,784,585, 3,792,010, 3,797,499, 3,839,297, 3,846,382, 3,867,190, 3,875,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600, and 2,102,827, D. K. Gilding et al., "Biodegradable polymers for use in surgery-polyglycolic/poly (lactic acid) homo-and copolymers: 1," *Polymer*, Volume 20, pages 1459–1464 (1979), and D. F. Williams (ed.), *Biocompatibility of Clinical Implant Materials*, Volume II, chapter 9: "Biodegradable Polymers" (1981). All of the foregoing documents are hereby incorporated by reference. Some of the foregoing documents listed mention or discuss annealing, heat-treating, or post-treating surgical articles containing the lactide/glycolide/related compound polymers or copolymers. See, e.g., U.S. Pat. Nos. 3,422,181, 3,626, 948, 3,636,956, 3,772,420, 3,792,010, 3,797,499, 3,839,297, 3,878,284, 4,137,921, 4,157,437, 4,243,775, 4,300,565, U.K. Pat. or Appln. Nos. 1,332,505, 1,414,600, and 2,102, 827, and U.S. Pat. Nos. 4,137,921, 4,157,437, 4,243,775, and 4,300,565.

In U.S. Pat. No. 4,744,365 it was found that certain two-phase compositions derived from lactide and glycolide in which lactide moieties predominate, have a remarkable and unexpected balance of desirable properties. Those properties include lack of brittleness and the ability to be injection molded and annealed. The properties of the composition make it possible to injection mold surgical devices (e.g., staples, clips) from the composition and to anneal those devices to obtain devices having a remarkable and unexpected balance of desirable properties. As compared to a substantially amorphous, one-phase poly(lactide/glycolide) device of a given composition, the annealed, two-phase device of the same overall composition has a much higher distortion temperature but essentially the same in vivo rate of loss of tensile strength. Thus, the compositions of U.S. Pat. No. 4,744,365 make it possible to increase the resistance to thermal distortion of poly(lactide/glycolide) surgical devices without adversely affecting their rate of loss of tensile strength. More particularly, the compositions of U.S. Pat. No. 4,744,365 comprise a multi-phase polymeric composition derived from lactide and glycolide, the first phase having about 0 to about 25% m glycolide moieties and about 75 to about 100% m lactide moieties and the other phases having glycolide and lactide moieties in amounts such that the composition overall has up to 45% m glycolide moieities, wherein the first phase constitutes at least 50% (and preferably not more than about 95%) by weight of the composition.

In addition to the afore-recited patents and other documents which disclose polymers and copolymers of, and surgical devices made from lactide and glycolide, other patents disclose surgical devices prepared from copolymers of lactide or glycolide and other monomers including caprolactone or trimethylene carbonate. Such patents include U.S. Pat. Nos. 4,700,704, 4,605,730 and 4,643,734. More particularly, U.S. Pat. Nos. 4,605,730 and 4,700,704 disclose copolymers of epsilon-caprolactone and glycolide useful in making surgical articles and particularly surgical sutures having low Young's modulus. In addition to the afore-recited patents, U.S. Pat. No. 4,624,256 discloses the utilization of high molecular weight caprolactone polymers as coatings for surgical sutures, while U.S. Pat. No. 4,429, 080 discloses surgical articles manufactured from triblock copolymers prepared from copolymerizing glycolide with trimethylene carbonate.

SUMMARY OF THE INVENTION

It is one object of the present invention to provide novel polymer compositions useful for the manufacture of surgical devices.

It is another object of this invention to provide polymer compositions which are comprised of novel blends of two or more polymers.

It is still another object of the present invention to provide absorbable surgical devices having improved mechanical properties which are manufactured from the novel polymer compositions of the invention.

These and other objects are accomplished herein by providing an absorbable polymeric composition, suitable for the manufacture of surgical devices, comprising a blend of:

(a) polymer selected from the group consisting of glycolide homopolymer, lactide homopolymer, a mixture of glycolide homopolymer and lactide homopolymer and glycolide/lactide copolymer; and (b) from about 1 weight percent to about 50 weight percent of a polymer selected from the group consisting of polycaprolactone homopolymer, polytrimethylene carbonate homopolymer, copolymers of caprolactone and lactide, copolymers of caprolactone and glycolide, copolymers of trimethylene carbonate and lactide, copolymers of trimethylene carbonate and glycolide, copolymers of caprolactone, glycolide and lactide, copolymers of trimethylene carbonate, glycolide and lactide and mixtures thereof, based on the total weight of the blend.

Other objects of the invention are achieved herein by providing absorbable surgical devices derived from the afore-described polymer blend compositions of the present invention.

DETAILED DESCRIPTION OF THE INVENTION

Copending U.S. patent application Ser. No. 07/654,234 filed on Feb. 12, 1991 discloses a bioabsorbable reinforced composite material and method for the production thereof, wherein a component of the composite material may comprise a blend of homopolymers or copolymers of glycolide and lactide and polycaprolactone, and/or polytrimethylene carbonate.

In accordance with the present invention, it has now been found that absorbable surgical devices manufactured from these blends comprised of glycolide homopolymer, lactide homopolymer, glycolide/lactide copolymer or mixtures thereof and polycaprolactone homopolymer, polytrimethylene carbonate homopolymer and/or copolymers of caprolactone or trimethylene carbonate and glycolide and/or lactide, wherein the caprolactone or the trimethylene carbonate is the predominant monomer, possess improved physical and mechanical properties in comparison with surgical devices derived from glycolide or lactide homopolymer or glycolide/lactide copolymer alone.

More particularly, surgical devices prepared from the polymer blends of the present invention comprising glycolide or lactide homopolymer or glycolide/lactide copolymer and polycaprolactone or polytrimethylene carbonate homopolymer and/or copolymers of caprolactone or trimethylene carbonate and glycolide and/or lactide, wherein the caprolactone or the trimethylene carbonate is the predominant monomer (i.e. greater than 50 mole percent preferably at least 80 mole percent), are found to exhibit improved impact resistance, improved crazing properties and improved cyclic flexibility, both when annealed and non-annealed.

The novel polymer compositions of the present invention are blends of at least two polymers one of which is polycaprolactone homopolymer or polytrimethylene carbonate homopolymer or copolymer of polycaprolactone and glycolide and/or lactide or copolymer of trimethylene carbonate and glycolide and/or lactide or a mixture thereof.

In particular, the novel blends of the present invention comprise polycaprolactone homopolymer or polytrimethylene carbonate homopolymer or copolymer of polycaprolactone and glycolide and/or lactide or copolymer of trimethylene carbonate and glycolide and/or lactide or mixtures thereof and a polymer selected from a glycolide homopolymer, a blend of a glycolide homopolymer and a lactide homopolymer, a glycolide/lactide copolymer or mixtures thereof.

For the glycolide homopolymer and lactide homopolymer or glycolide/lactide copolymer employed, the proportion of glycolide in relation to lactide in the composition can vary depending upon the physical properties desired. For example, if the proportion of lactide is too high, the absorption time of a surgical implant device derived therefrom may be too long and if the glycolide proportion is too high, the breaking strength (tensile strength) retention upon implantation in the body of the device may be unacceptable. Typically acceptable results are achieved when up to about 50% glycolide, in relation to the amount of lactide, is used. Thus, preferred copolymers useful in the practice of the present invention are those comprising about 18/82 glycolide/lactide (mole percent), 10/90 glycolide/lactide (mole percent) 35/65 glycolide/lactide (mole percent) and 42/58 glycolide/lactide (mole percent).

The glycolide homopolymers, lactide homopolymers and glycolide/lactide copolymers employed in the blends of the present invention are known materials and are readily synthesized by known methods. Generally, the glycolide and/or lactide homopolymer and glycolide/lactide copolymers employed in the blends of the present invention have a molecular weight such that they have an inherent viscosity of from about 0.9 to about 2.0 dl/g and preferably about 1.0 to about 1.8 dl/g measured at 30° C. at a concentration of 0.25 g/dl in chloroform or hexafluoroisopropanol (HFIP). Particularly preferred glycolide/lactide copolymer for the purposes of the present invention are the two-phase or multi-phase compositions disclosed in U.S. Pat. No. 4,744,365, the entire contents of which is incorporated by reference herein.

The polycaprolactone homopolymers and copolymers employed in polymer blends of the present invention are also well known and commercially available materials. For the purposes of the present invention, polycaprolactone homopolymers or copolymers having an inherent viscosity of from about 0.8 to about 2.5 dl/g measured at 30° C. and a concentration of 0.25 g/dl in chloroform or HFIP are generally employed.

The polytrimethylene carbonate homopolymers and copolymers used in the practice of the present invention are also well known and commercially available materials. For purposes of the present invention polytrimethylene carbonate homopolymers having an inherent viscosity of from about 0.8 to about 2.5 dl/g measured at 30° C. and a concentration of 0.25 g/dl in chloroform or HFIP are generally used.

Copolymerization of caprolactone or trimethylene carbonate with glycolide and/or lactide has been found to facilitate handling of the caprolactone or trimethylene carbonate, e.g., processing through and removal from extrusion equipment.

The polymer blends of the present invention are typically prepared by melt blending the components of the blend. The glycolide and/or lactide homopolymer or mixture thereof or the glycolide/lactide copolymer is used in the blend in a major amount, that is, from about 50 to about 99 weight percent of the total weight of the blend, the remainder, i.e. from about 1 to about 50 weight percent, comprising polycaprolactone homopolymer and/or copolymer and/or polytrimethylene carbonate homopolymer and/or copolymer. Melt blending is typically carried out at a temperature of 170° C. to 200° C. for a time sufficient to liquify the components, the time being dependent on such parameters as vessel, heat transfer properties, and presence and extent of blending. Typically, melt time ranges from a few minutes for small amounts of polymer to a couple of hours for large quantities.

It has also been found herein that surgical devices manufactured from the blends of the present invention possess the excellent afore-described physical properties whether or not annealed.

Whichever polymer blend of the present invention is used, the absorbable surgical devices are made, preferably, by injection molding the blend at temperatures in the range of from about 300 to about 400° F. at an injection molding pressure of, for example, about 1,500 psi. Typically, the feed for the injection molding apparatus is a melt blend of the two polymers in pellet form. The polymers should be quite dry when being injection molded in order to avoid hydrolytic degradation during processing. After molding, the surgical devices can be packaged and sterilized by conventional procedures. It may be desirable to anneal the devices to remove residual stresses and strains, to stabilize the shape of the device, and to reduce or eliminate defects in the piece. Annealing typically comprises reheating the polymeric device to above its glass transition temperature where chain mobility is greatest, and then slowly and gradually cooling the device to avoid reintroducing. Procedures, conditions and apparatus for annealing polymeric structures are well known in the art.

A wide variety of absorbable surgical devices can be manufactured from the polymer blends of the present invention. These include fasteners, such as staples, clips and the like and other implant devices, such as pins, bone screws, or the like.

As expressed hereinbefore, the surgical devices of the present invention exhibit excellent in vivo cyclic flex performance, a mechanical property which is highly desired in surgical devices and in particular, for example, in surgical implant devices, such as surgical fastener/retainer systems which, after implantation, are subject to a variety of forces and often undergo repeated flexing.

Furthermore, surgical devices manufactured from the novel polymer blends of the present invention exhibit improved impact resistance as well as improved crazing resistance. Crazing may be defined as surface cracking of the material as contrasted with impact resistance which is more a measure of a material's tendency to allow crack propagation. Crazing may be observed visually, such as for example, a polymeric article which is flexed will evidence crazing by fogging of an otherwise clear or transparent material. In surgical applications, once a surgical article crazes, although the article may continue to function for a limited period, the article may not exhibit the desired strength. Thus, a material with a more limited tendency to craze when fabricated, for example, into a surgical implant device such as a bone screw, would permit the bone screw to be torqued to a greater extent without a likelihood that the screw would craze and thereby become ineffective for its intended purpose.

The examples below are illustrative of the blends of the present invention and surgical devices derived therefrom.

EXAMPLE 1

A copolymer of glycolide and lactide is prepared as follows:

Hydroxyacetic acid (glycolic acid) is heated under nitrogen to 180° C. to remove impurities such as water. Pressure is then reduced and heating is continued for two hours to yield a prepolymer of polyglycolic acid, which is recovered and powdered.

The prepolymer is heated in the presence of $Sb_2O_3$ at 275° C. under low pressure with an argon purge and stirring. The prepolymer cracks and glycolide is distilled over and recovered in a cold vacuum receiver. Preferably, the glycolide is purified by conventional techniques, such as distillation, crystallization, and sublimation.

L-lactide is used alone or in combination with a small amount of the DL racemer. L-lactide is purified by crystallization from toluene solution. The DL racemer, if used, is purified by crystallization from ethyl acetate.

A mixture of the purified glycolide (18 mole percent) and lactide (82 mole percent) is charged to a reactor under an argon blanket. A solution of stannous octoate catalyst in diethyl ether is added to give 0.02% w. of catalyst, based on the total weight of glycolide and lactide. The reactor is further purged with argon and held at 5 psi while heating to 170°–175° C. Pressure and temperature are maintained for six hours.

The reaction product is isolated, comminuted, and treated to remove residual reactants. Any method capable of removing the unreacted monomers from the crude reaction product may be used. A preferred purification procedure is as follows.

After comminution, the crude reaction product is contacted with ethyl ether for about 72 hours in a Soxhlet-type extractor to remove unreacted monomer. Typically, 4–10% of the starting monomers remain unreacted, and the glass transition temperature of the crude copolymer is approximately 50° C. Removal of unreacted monomers raises the glass transition temperature. As will be understood by one skilled in the art, the composition of the copolymer may differ slightly from the composition of the starting monomeric mixture because the lactide and glycolide are not of equal reactivity.

After the extraction period, the partially purified copolymer is slowly heated under vacuum from ambient temperature to 140° C. over a period of about 48 hours. The slow rate of heating is desirable to prevent melting (strictly speaking, flowing together) of the co-polymer particles and to remove any water present. Desirably, dry inert gas is used to purge the system, and occasionally the heating step may require more than 48 hours to reach the desired glass transition temperature. The combination of slow heating and purging with dry gas removes any residual solvent (ethyl ether) present, thereby raising the glass transition temperature.

After removal of unreacted monomers (and of solvent, if solvent extraction is used), the purified copolymer is further dried if it was not dried enough in the monomer removal step and, in any event, stored to keep it dry.

Trimethylene carbonate is polymerized in a reactor at 160° C. with a stannous octoate catalyst. The polytrimethylene carbonate so formed is melt blended with the glycolide/lactide copolymer (18/82) described above in the reactor at a temperature of 190° C. and at a weight ratio of 25:75. The blended polymer is extruded, ground, extracted with ether, and dried in accordance with known procedures.

Surgical devices fabricated from this blended polymer exhibit excellent physical properties, including good impact resistance, resistance to crazing and cyclic flexibility.

EXAMPLE 2

A glycolide/lactide copolymer (18/82 mole ratio) prepared as described in Example 1 is melt blended with a polycaprolactone homopolymer at weight ratios of 85:15 and 80:20 in a reactor at a temperature of 190° C. The blended polymer is extruded, ground, extracted with ether, and dried, as are known in the art.

The melt blended polymers are injection molded at a temperature of 130° C. to 140° C. at an injection molding pressure, e.g., 1,500 to 1,750 psi, to form a series of test plates measuring 2.2 inch ×2.7 inch×0.070 inch. One portion of the test plates are annealed at an annealing temperature of about 85° C. to 100° C. for 12 to 16 hours to remove internal stresses. A second portion of the test plates are not annealed. Control test plates are also injection molded from the glycolide/lactide copolymer described in Example 1, none of which are annealed.

EXAMPLE 3

The test plates injection molded as described in Example 2 are tested for impact resistance using a standard dart impact tester. The test plates are designated as follows:
Control: glycolide/lactide copolymer (18/82); unannealed Sample 1: glycolide/lactide copolymer (18/82) blended with polycaprolactone at a weight ratio of 85:15; unannealed
Sample 2: glycolide/lactide copolymer (18/82) blended with polycaprolactone at a weight ratio of 85:15; annealed
Sample 3: glycolide/lactide copolymer (18/82) blended with polycaprolactone at a weight ratio of 80:20; unannealed
Sample 4: glycolide/lactide copolymer (18/82) blended with polycaprolactone at a weight ratio of 80:20; annealed The results of the impact tests are set forth in the following Table I:

TABLE I

| Force (in-lb) | Control | Sample 1 | Sample 2 | Sample 3 | Sample 4 |
| --- | --- | --- | --- | --- | --- |
| 10 | 4 | 4 | 4 | 4 | 3 |
| 20 | 6 | 4 | 4 | 4 | 3 |
| 30 |   |   | 6 |   |   |
| 40 |   |   |   | 5 | 4 |

Mode of Failure: 1. No effect; 2. Slight fractures; 3. Indentation with some crazing; 4. Cracks at point of contact; 5. Hole punched at point of contact; 6. Shattered.

These results show that the polymeric blends of the present invention exhibit improved impact resistance as compared to a non-blended control, i.e., a glycolide/lactide copolymer without added polycaprolactone. In addition, the test plates for Samples 1–4 exhibit improved resistance to crazing. Improved cyclic flex performance is also to be expected.

EXAMPLE 4

A two-phase polymeric composition comprising glycolide and lactide is prepared according to the procedure described in U.S. Pat. No. 4,744,365. A first monomer mixture of glycolide and lactide at a mole ratio of 10:90 is polymerized in the presence of a stannous octate catalyst until the polymerization is substantially complete. To this glycolide/lactide copolymer is added a second monomer mixture consisting of additional glycolide, such mixture being added in sufficient quantity that the final mole ratio of the two-phase polymeric composition is 35:65 glycolide to lactide. After the additional glycolide polymerizes with the glycolide/lactide copolymer, the two-phase polymer composition is ground, dried and ether extracted in accordance with known procedures.

Polycaprolactone is combined with the two-phase glycolide/lactide polymeric composition at mole ratios of 5:95 and 10:90, melt blended therewith at a temperature of 170° C. to 200° C. and the resulting blends are pelletized for subsequent use as described below.

The pellets of melt blended polymer are injection molded at a temperature of 130° C. to 140° C. at an injection molding pressure, e.g., 1,500 to 1,750 psi, to form a series of test plates measuring 2.2 inch ×2.7 inch ×0.070 inch. Control test plates are also injection molded from the two-phase glycolide/lactide polymeric compositions. One portion of the test plates are annealed at an annealing temperature of about 85° C. to 100° C. for 12 to 16 hours to remove internal stresses. A second portion of the test plates are not annealed.

The test plates are tested for impact resistance using a standard falling dart impact tester. The test plates are designated as follows:
Control 1: two-phase glycolide/lactide polymer (35/65); unannealed
Control 2: two-phase glycolide/lactide polymer (35/65); annealed
Sample 1: two-phase glycolide/lactide polymer (35/65) blended with polycaprolactone at a weight ratio of 95:5; unannealed
Sample 2: two-phase glycolide/lactide polymer (35/65) blended with polycaprolactone at a weight ratio of 95:5; annealed
Sample 3: two-phase glycolide/lactide polymer (35/65) blended with polycaprolactone at a weight ratio of 90:10; unannealed
Sample 4: two-phase glycolide/lactide polymer (35/65) blended with polycaprolactone at a weight ratio of 90:10; annealed The results of the impact tests are set forth in the following Table II:

TABLE II

| Force (in-lb) | Control 1 | Control 2 | Sample 1 | Sample 2 | Sample 3 | Sample 4 |
| --- | --- | --- | --- | --- | --- | --- |
| 10 | 4 5 | 4 |   |   |   |   |
| 20 | 5 | 4 5 | 4 | 2 4 2 | 2 | 2 |
| 30 |   | 5 |   |   |   |   |
| 40 | 5 6 | 6 |   | 4 | 3 | 3 |
| 50 | 5 6 |   |   |   |   |   |
| 60 | 6 | 6 |   | 4 4 | 3 | 3 |
| 80 |   |   |   | 4 4 | 3 3 | 3 3 |

These results show that the polymeric blends of the present invention exhibit improved impact resistance as compared to non-blended controls, i.e., glycolide/lactide polymers without added polycaprolactone. In addition, the test plates for Samples 1–4 exhibit improved resistance to crazing. Improved cyclic flex performance is also to be expected.

What is claimed is:

1. A polymer composition, useful in the production of improved absorbable surgical devices, said polymer composition comprising a blend of:
   a) a polymer selected from the group consisting of glycolide homopolymer, lactide homopolymer, a mixture of glycolide homopolymer and lactide homopolymer, a glycolide/lactide copolymer and mixtures thereof; and
   b) from about 1 to about 50 weight percent, based on the total weight of the blend, of a polymer selected from the group consisting of copolymers of caprolactone and lactide, copolymers of caprolactone and glycolide, copolymers of trimethylene carbonate and lactide, copolymers of trimethylene carbonate and glycolide, copolymers of caprolactone, glycolide and lactide, copolymers of trimethylene carbonate, glycolide and lactide and mixtures thereof.

2. The polymer composition of claim 1 wherein component (a) is a copolymer of glycolide and lactide.

3. The polymer composition of claim 2 wherein said copolymer comprises up to about 50 mole percent glycolide.

4. The polymer composition of claim 1 wherein component b) is present in the blend in an amount of from about 5 to about 10 weight percent, based on the total weight of the blend.

5. The polymer composition of claim 2 wherein the glycolide/lactide copolymer comprises a multi-phase composition, the first phase having from about 0 to about 25 mole percent glycolide moieties and about 75 to about 100 mole percent lactide moieties and the other phase or phases having glycolide and lactide moieties in amounts such that the composition overall has up to 45 mole percent glycolide moieties, wherein the first-phase constitutes at least 50% by weight of copolymer.

6. The polymer composition of claim 1 wherein the glycolide/lactide copolymer has an inherent viscosity of from about 0.9 to about 2.0 dl/g measured at 30° C. at a concentration of 0.25 g/dl in chloroform or hexafluoroisopropanol.

7. An absorbable surgical device derived from a polymer composition comprising a blend of:

(a) a polymer selected from the group consisting of glycolide homopolymer, lactide homopolymer, a mixture of glycolide homopolymer and lactide homopolymer, a glycolide/lactide copolymer and mixtures thereof; and (b) from about 1 to about 50 weight percent, based on the total weight of the blend, of a polymer selected from the group consisting of copolymers of caprolactone and lactide, copolymers of caprolactone and glycolide, copolymers of trimethylene carbonate and lactide, copolymers of trimethylene carbonate and glycolide, copolymers of caprolactone, glycolide and lactide, copolymers of trimethylene carbonate, glycolide and lactide and mixtures thereof.

8. The absorbable surgical device of claim 7 selected from the group consisting of a fastener, pin and bone screw.

* * * * *